(12) United States Patent
Rockley et al.

(10) Patent No.: US 7,883,521 B2
(45) Date of Patent: *Feb. 8, 2011

(54) MULTI-FUNCTIONAL SECOND INSTRUMENT FOR CATARACT REMOVAL

(75) Inventors: Paul W. Rockley, Laguna Niguel, CA (US); Randall J. Olson, Salt Lake City, UT (US)

(73) Assignee: Abbott Medical Optics Inc., Santa Ana, CA (US)

( * ) Notice: Subject to any disclaimer, the term of this patent is extended or adjusted under 35 U.S.C. 154(b) by 1499 days.

This patent is subject to a terminal disclaimer.

(21) Appl. No.: 10/958,971

(22) Filed: Oct. 5, 2004

(65) Prior Publication Data

US 2005/0043671 A1 Feb. 24, 2005

Related U.S. Application Data

(63) Continuation of application No. 09/973,139, filed on Oct. 9, 2001, now Pat. No. 6,830,555.

(51) Int. Cl.
*A61B 17/32* (2006.01)

(52) U.S. Cl. .................................. 606/169; 604/22
(58) Field of Classification Search ................. 606/4–6, 606/166, 167, 169, 107, 170; 604/20, 22
See application file for complete search history.

(56) References Cited

U.S. PATENT DOCUMENTS

| | | | | |
|---|---|---|---|---|
| 3,736,938 A | * | 6/1973 | Evvard et al. | 606/169 |
| 5,154,696 A | * | 10/1992 | Shearing | 604/22 |
| 5,562,640 A | * | 10/1996 | McCabe et al. | 604/541 |
| 6,017,354 A | * | 1/2000 | Culp et al. | 606/170 |
| 6,371,934 B1 | * | 4/2002 | Jackson et al. | 604/35 |
| 6,830,555 B2 | * | 12/2004 | Rockley et al. | 604/22 |

* cited by examiner

*Primary Examiner*—Michael J Milano
*Assistant Examiner*—Victor X Nguyen

(57) ABSTRACT

Apparatus for the removal of lens tissue includes a first instrument for inserting into a lens capsule and removing a cataract therein, the first instrument including a lumen for aspiration of cataract tissue and irrigation fluid from the lens capsule and manipulate the cataract until cataract is removed. The second instrument includes an irrigation port for introducing the irrigation fluid into the lens capsule.

6 Claims, 2 Drawing Sheets

MULTI-FUNCTIONAL SECOND INSTRUMENT FOR CATARACT REMOVAL

The present application is a continuation application of U.S. patent application Ser. No. 09/973,139, filed Oct. 9, 2001, now U.S. Pat. No. 6,830,555.

The present invention generally relates to surgical instruments, and more particularly, relates to apparatus which provides for improved irrigation and reduced risk of corneal or sclera tissue damage during cataract removal.

Cataracts cause the lens of an eye to become clouded, and a common practice to alleviate this condition is by surgically removing the cataractic lens and replacing it with an artificial intraocular lens.

Early lens removal was effected through manual extraction which required a wound of about 12 mm in length. This large opening can result in corneal or sclera tissue damage.

Phacoemulsification, on the other hand, enables the removal of a cataractic lens through a much smaller incision, for example, between about 2.5 to about 4 mm. In this procedure, a needle is inserted through the incision into a lens capsule and the needle is vibrated to mechanically emulsify the lens. It is often desirable to utilize a second tool in order to manipulate the lens toward and around the phacoemulsification needle in order to more effectively emulsify the lens. Once fragmented or emulsified, the lens material is aspirated through a lumen through the phacoemulsification needle.

Heretofore, while emulsifying the lens and aspirating lens fragments, a simultaneous flow of irrigation fluid into the lens capsule has been provided around the needle through an annulus established by a sleeve concentrically disposed over the needle. This flow of liquid into the eye is necessary to prevent collapse of the interior chamber of the eye during aspiration. In addition, the irrigation fluid cools the needle in order to prevent any thermal damage of the corneal or sclera tissue. While the sleeve surrounding a phacoemulsification needle provides the important function of establishing an annulus for introducing irrigation fluid into the lens capsule it also enlarges the overall diameter of the sleeve needle for which an incision must be made.

In addition, when irrigation fluid is introduced proximate the emulsifying needle tip, the immediate area in front of the needle is roiled. This occurs because of the counter-current flow of fluid being aspirated by the needle itself and the irrigation fluid being introduced over the surface of the needle. Needle vibration causes a cloud of debris which is roiled by the incoming infusion fluid which lessens the physicians visual acuity of the end of the needle which can slow the procedure. This roiling also pushes nuclear fragments away from the needle rendering the procedure less efficient.

The present invention overcomes the drawbacks of a sleeved phacoemulsification needle.

SUMMARY OF THE INVENTION

Apparatus in accordance with the present invention includes a first instrument for inserting into a lens capsule and removing a cataract therein, the needle including a lumen therethrough for aspiration of lens tissue and irrigation fluid from said lens capsule through a primary aspiration port defined by an end of said lumen and a second instrument for inserting into the lens capsule and manipulating the cataract as the cataract is being removed, said second instrument having an irrigation port for introducing the irrigation fluid into said lens capsule.

More specifically, the second instrument may include a tip, such as a hook or blade, attached to a shaft for manipulating the cataract and the shaft includes a shaft lumen for delivery the irrigation fluid to the irrigation port. Alternatively, the second instrument may include a conduit attached to the shaft, for delivering the irrigation fluid to the irrigation port. Further, a plurality of irrigation ports may be provided, each in fluid communication with the shaft lumen or conduit.

More specifically, the first instrument may include a sonic or ultrasonic device needle for emulsifying the lens tissue. In this instance, the needle includes a lumen for aspiration of emulsifying lens tissue and aspiration flow from the lens capsule.

BRIEF DESCRIPTION OF THE DRAWINGS

The advantages and features of the present invention will be better understood by the following description when considered in conjunction with the accompanying drawings in which.

DETAILED DESCRIPTION

Figure 1:
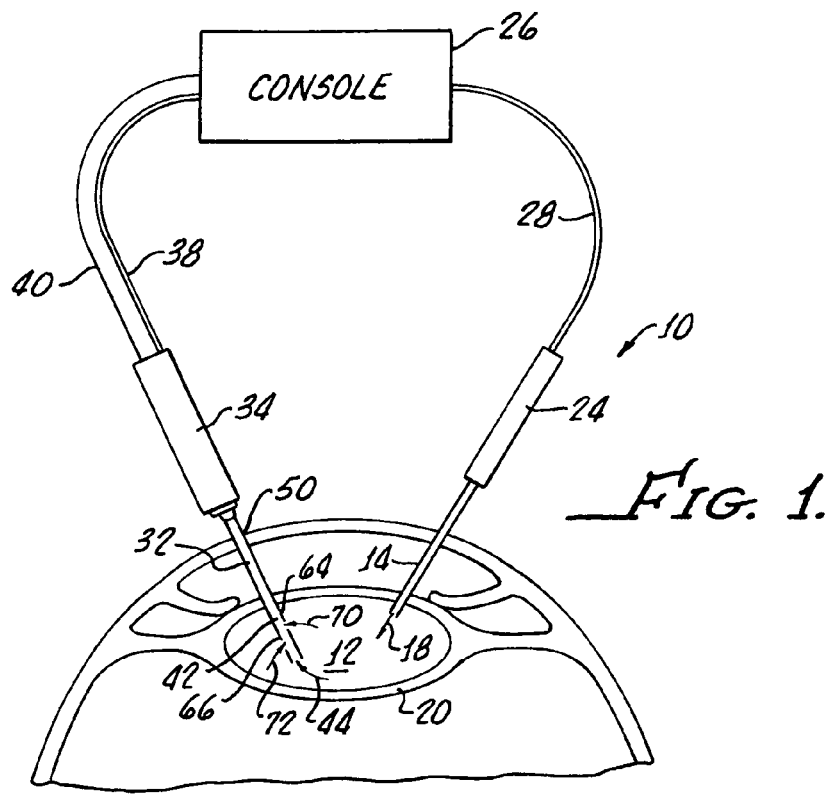
FIG. 1 is a diagram of apparatus in accordance with the present invention generally showing a first needle for introducing an irrigation fluid into a lens capsule through a handpiece from an operating console along with a second vibrated needle for inserting into the lens capsule and operated by a phacoemulsification handpiece connected to an aspiration line and controlled by the console through an ultrasonic power line.

With reference to FIG. 1, there is shown apparatus 10 for the removal of lens tissue 12 which includes a first needle 14 for introducing an irrigation fluid indicated by the arrow 18 into a lens capsule 20.

Manipulation of the needle 14 within the lens capsule 20 is effected through a handpiece 24 which communicates to a control console 26 through an irrigation line 28. The control console 26 may be of any suitable type as for example, one manufactured by Allergan, Inc., under the trade name Sovereign.

Figure 2:
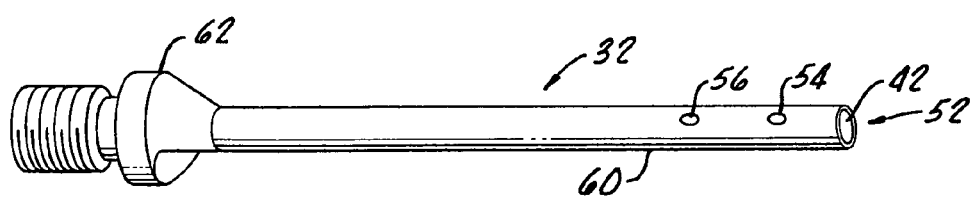
FIG. 2 is a view of the vibrated needle shown in FIG. 1 showing a primary aspiration port along with two secondary aspiration ports formed in the needle in a spaced apart distance from the primary aspiration port.

Also shown in FIG. 1, as well as in FIG. 2, is a second needle 32 which is ultrasonically vibrated by a handpiece 34. Any suitable handpiece may be utilized such as for example, one sold by Allergan, Inc., under the trade name Sovereign. The handpiece 34 is interconnected to the console 26 and control thereby through an aspiration line 38 and a power line 40 for controlling ultrasonic power delivered to the needle 32 by the handpiece 34.

The second needle 32 fragments or emulsifies the cataractic lens 12 which is then aspirated along with irrigation fluid through a lumen 42 in the needle 32 as indicated by the arrow 44. Manipulation of the irrigating needle 14 is effective in enabling more efficient removal of the cataractic lens 12 as the fluid is now a manipulation tool, moving fragments of lens 12 to the needle 32.

Because the needle 32 does not include a conventional sleeve (not shown in FIGS. 1 and 2) a smaller incision or wound 50 is required. The wound size may be as small as 0.8 mm which is to be compared with conventional sleeved needles (not shown) which would require a slit or wound opening, of about 2.5 to 3 mm (or larger).

As more clearly shown in FIG. 2, the needle 32 includes a primary aspiration port 52 defined by the lumen 42 and one or more secondary aspiration ports 54, 56 disposed along a length 60 of the needle 32 between the primary aspiration port 52 and a hub 62 for attachment of the needle 32 to the handpiece 34.

The secondary aspiration ports 54, 56 may be spaced apart axially from the primary aspiration port and one another as shown in FIG. 2 or, alternatively, as shown in FIG. 1, aspiration ports 64, 66 may be disposed along the needle 32 in a spaced apart radial relationship with one another resulting in aspiration of fluid from the lens capsule 20 in opposing direction as indicated by the arrows 70, 72.

The secondary aspiration ports 54, 56, 64, 66 also provide an important function in maintaining the fluid flow through the needle should the primary aspiration port 52 become occluded. This insures cooling of the needle 32 to prevent overheating thereof. Preferably, the secondary aspiration ports 54, 56, 64, 66 are disposed within 6 mm of the primary aspiration port to insure that their aspirating functionality is performed within the lens capsule 20. In order to insure that the majority of aspiration occurs through the primary aspiration port, it is preferred that the total cross-sectional area of the secondary aspiration ports 54, 56, 64, 66 be no more than 10% of the cross-sectional area of the primary aspiration port 52.

Figure 3:
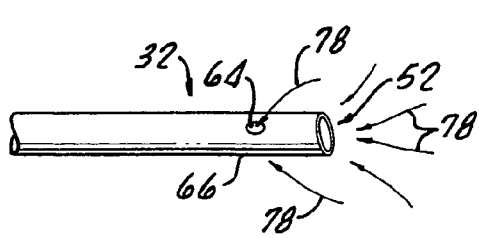
FIG. 3 is a view of the needle tip shown in FIG. 2 illustrating non-turbulent aspiration of lens tissue and irrigation fluid.
Figure 4:
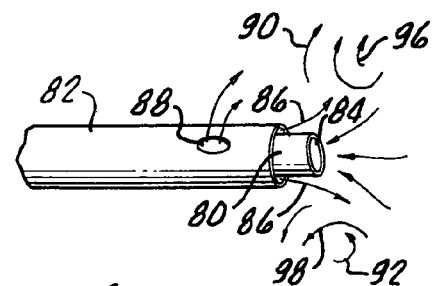
FIG. 4 is a similar view of a prior art sleeved needle top illustrating turbulence or roiling of fluid in front of the needle tip caused by countercurrent fluid flow with results in a cloud of emulsified lens tissue and repulsion of the same.

The advantages of the unsleeved needle 32 are more clearly understood with reference to FIGS. 3 and 4. FIG. 3 illustrates smooth laminar flow of aspiration fluid as shown by the arrows 78 into the primary aspiration port 52 and secondary aspiration ports 64, 66.

This is to be contrasted with a conventional phacoemulsification needle tip 80 which is surrounded by a sleeve 82 for the introduction of irrigation fluid proximate to an aspiration port 84 as indicated by the arrows 86. The sleeve 82 also has side holes 88 for irrigation outflow.

As illustrated, aspiration of fluid as indicated by the arrows 90, 92 may be partially diverted from the port 84 before entering which causes a roiling of the fluid indicated by the arrows 96, 98. This roiling of fluid causes a "milky cloud" to appear proximate the needle tip 80 and pushes lens fragments away which interferes with the physician acuity of the needle tip 80 which prevents efficient phacoemulsification of lens tissue, not shown in FIG. 4.

Figure 5:
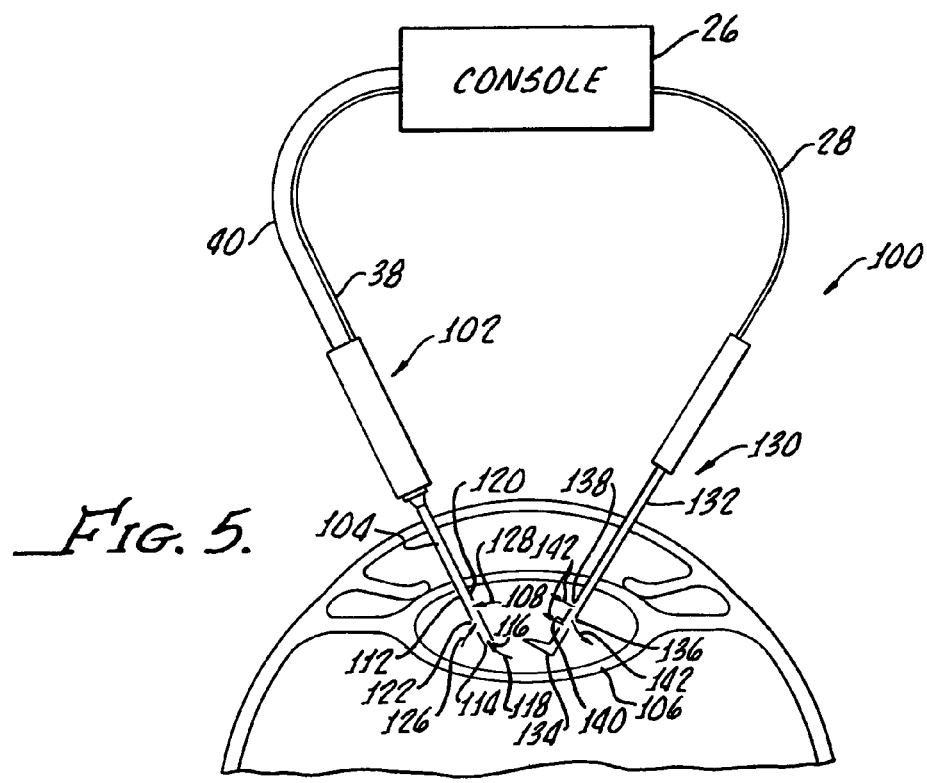
FIG. 5 is a diagram of alternative apparatus in accordance with the present invention generally showing a first instrument including a vibrated needle for inserting into a lens capsule and operation by a handpiece connected to an aspiration line and controlled by a console through a power line along with a second instrument for inserting into the lens capsule for manipulating a cataract during removal thereof and for providing irrigation fluid to the lens capsule.

With reference to FIG. 5, there is shown in an alternative embodiment 100 in accordance with the present invention, in reference, characters refer to a similar or substantially identical elements hereinabove discussed in connection with the embodiment 10 shown in FIG. 1.

Embodiment 100 includes a second instrument 102 which includes a vibrated needle 104 for inserting into a lens capsule 106 for removing a cataract 108 therein. The needle 104 includes a lumen 112 therethrough for aspiration of cataract tissue from the lens through a primary aspiration port 114 defined by an end 116 of the needle 104, this aspiration is indicated by the arrow 118. Preferably, second aspiration ports 120, 122 are provided in the needle 112 for aspirating cataractic tissue, as well as irrigation fluid, from the lens capsule 106 as indicated by the arrows 126, 128.

A first instrument 130, which includes a shaft 132 and tool tip 134, is inserted into the lens capsule 106 for manipulating the cataract 108 as the cataract 108 is being emulsified by the needle 104.

The first instrument 130 includes one or more irrigation ports 136, 138, 140 for introducing irrigation fluid into the eye capsule 106 as indicated by the arrows 140.

Figure 6:
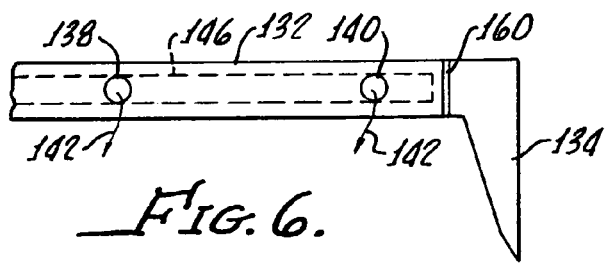
FIG. 6 is an enlarged representation of a second instrument tip illustrating introduction of irrigation fluid through irrigation ports from a lumen in a shaft supporting a tool tip.

An enlarged view of the tool tip 34 and shaft 132 are shown in FIG. 6. Irrigation fluid is provided to the ports 138, 140 shown in FIG. 6 through a lumen 146 within the shaft 132. Alternatively, as shown in FIG. 7, the tool tip 34 may be supported by a solid shaft 148 and a separate conduit 150 may be utilized to provide irrigation fluid to irrigation ports 152, 154.

Figure 8:
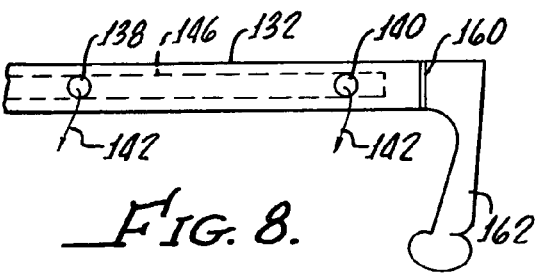
FIG. 8 is similar to FIG. 6 illustrating a different tool tip which may be fixed to a separate shaft or used as a replaceable tip.
Figure 7:
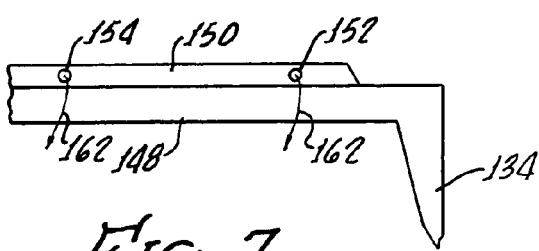
FIG. 7 is similar to FIG. 6 illustrating the introduction of irrigation fluid through irrigation ports from a conduit adhered to a shaft supporting a tool tip.

The tool tip 134 may be of any suitable type, such as for example, a hook or a blade, for manipulation of the cataractic tissue 108 and may be fixed to a shaft 148 as shown in FIG. 7 or removably coupled to a shaft 132 by a conventional coupling mechanism 160. When a coupler 160 is utilized, alternative tool tips 162, as shown in FIG. 8, may be attached to the shaft 132 by the user.

The irrigation ports 138, 140, 152, 154 are preferably spaced apart axially on the shaft 132, 148 respectively or, as illustrated in FIG. 5, there may be also space radially about the shaft. The size of the ports 138, 140, 152, 154 may be 0.6 to 1.5 mm in order to introduce irrigation fluid 164 at the rate of 20-60 cc/min. The irrigation port 138, 140, 152, 154 size and location is dependant upon surgeon technique and incision location.

Although there has been hereinabove described apparatus for the removal of lens tissue in accordance with the present invention for the purposes of illustrating in which the manner in which the invention may be used to an advantage, it will be appreciated that the invention is not limited thereto. Accordingly, any and all modifications, variations, or equivalent arrangements which may occur to those skilled in the art should be considered to be within the scope of the invention as defined in the appended claims.

What is claimed is:

1. Apparatus for the removal of lens tissue, said apparatus comprising:

a first instrument having a shaft insertable into a lens capsule and a manipulating tool tip, said first instrument having an irrigation port introducing irrigation fluid into said lens capsule; and a second instrument, including an unsleeved needle configured to ultrasonically vibrate and insertable into the lens capsule, the second instrument including a primary aspiration port and a lumen therethrough configured to aspirate emulsified cataract tissue and irrigation fluid from said lens capsule, the second instrument also including one or more secondary ports disposed along a length of the lumen and configured to aspirate emulsified cataract tissue, irrigation fluid, or both, said unsleeved vibrated needle having a diameter enabling insertion of said unsleeved vibrated needle through a wound opening of less than about 2 mm, wherein the first instrument and the second instrument are separate handpieces.

2. The apparatus according to claim 1 wherein said shaft includes an irrigation fluid delivery shaft lumen therethrough.

3. The apparatus according to claim 1 wherein said first instrument comprises a conduit, attached to said shaft, configured to deliver the irrigation fluid to said irrigation port.

4. The apparatus according to claim 1 wherein said first instrument comprises a plurality of irrigation delivery ports.

5. The apparatus of claim 1, wherein said one or more ports are disposed within 6 mm of the primary aspiration port.

6. The apparatus of claim 1, wherein said one or more ports have a cross-sectional area of no more than 10% of the cross-sectional area of the primary aspiration port.

* * * * *